(12) United States Patent
Williams

(10) Patent No.: US 6,353,146 B1
(45) Date of Patent: Mar. 5, 2002

(54) FIBROUS ARTICLES HAVING ODOR ADSORBTION ABILITY AND METHOD OF MAKING SAME

(75) Inventor: Karla E. Williams, Emerson, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/062,993

(22) Filed: Apr. 20, 1998

(51) Int. Cl.$^7$ .......................... A61F 13/15; A61F 13/20
(52) U.S. Cl. .............. 604/359; 604/358; 604/360; 604/367
(58) Field of Search ................ 604/359, 358, 604/360, 367

(56) References Cited

U.S. PATENT DOCUMENTS

| | | |
|---|---|---|
| 3,340,875 A | 9/1967 | Dudley et al. |
| 3,939,838 A | 2/1976 | Fujinami et al. |
| 3,948,257 A | 4/1976 | Bossak |
| 4,237,591 A | 12/1980 | Ginocchio |
| 4,289,513 A | 9/1981 | Brownhill et al. |
| 4,525,410 A | 6/1985 | Hagiwara et al. |
| 4,529,623 A | 7/1985 | Maggs |
| 4,547,195 A | 10/1985 | Jackson |
| 4,583,980 A | 4/1986 | Schneider et al. |
| 4,657,808 A | 4/1987 | Maggs |
| 4,724,242 A | 2/1988 | Vassileff |
| 4,743,237 A | 5/1988 | Sweere |
| 4,795,482 A | 1/1989 | Gioffre et al. |
| 4,826,497 A | 5/1989 | Marcus et al. |
| 5,019,062 A | 5/1991 | Ryan et al. |
| 5,037,412 A | 8/1991 | Tanzer et al. |
| 5,122,407 A | 6/1992 | Yeo et al. |
| 5,306,487 A | 4/1994 | Karapasha et al. |
| 5,342,333 A | 8/1994 | Tanzer et al. |
| 5,364,380 A | 11/1994 | Tanzer et al. |
| 5,407,442 A | 4/1995 | Karapasha |
| 5,429,628 A | 7/1995 | Trinh et al. |
| 5,580,851 A | 12/1996 | Trinh et al. |

FOREIGN PATENT DOCUMENTS

WO    WO 81/01643    * 12/1980

OTHER PUBLICATIONS

U.S. Statutory Invention Registration H1579 to Furio, published Aug. 6, 1996.

* cited by examiner

*Primary Examiner*—John G. Weiss
*Assistant Examiner*—Michele Kidwell
(74) *Attorney, Agent, or Firm*—Ohlandt, Greeley, Ruggiero & Perle, LLP

(57) ABSTRACT

There is provided a fibrous absorbent article for absorbing body fluids. The article includes a fibrous material suitable for absorbing the body fluids, and a molecular sieve disposed within the fibrous material to reduce odors from the body fluids. The molecular sieve is a natural zeolite of the clinoptilolite or chabasite species having an exchangeable cation.

17 Claims, 4 Drawing Sheets

ODOR ADSORPTION EFFICACY

ZEOLITE STRIP – 51g/m² ZEOLITE

| ZEOLITE (g) | AVERAGE % ADSORBED | STANDARD DEVIATION |
|---|---|---|
| 0.117 (3.56 IN²) | 98.0 | 1.7 |
| 0.088 (2.67 IN²) | 98.6 | 0.8 |
| 0.059 (1.78 IN²) | 97.8 | 0.6 |
| 0.029 (0.89 IN²) | 86.1 | 2.3 |
| 0.015 (0.44 IN²) | 53.3 | 3.0 |

ZEOLITE- (36.6%) LIQUID SUSPENSION

| ZEOLITE (g) | AVERAGE % ADSORBED | STANDARD DEVIATION |
|---|---|---|
| 0.011 (0.03g SLURRY/PAD) | 50.6 | 1.7 |
| 0.018 (0.05g SLURRY/PAD) | 95.0 | 1.8 |
| 0.026 (0.07g SLURRY/PAD) | 95.6 | 1.8 |
| 0.037 (0.10g SLURRY/PAD) | 97.0 | 2.5 |
| CONTROL (PAD) | 36.7 | 4.5 |

FIBROUS ARTICLES HAVING ODOR ADSORBTION ABILITY AND METHOD OF MAKING SAME

BACKGROUND OF THE INVENTION

1. Field of the Invention

This invention relates to fibrous articles intended for absorption of body fluids and, in particular, to tampons and similar catamenial devices. Such fibrous articles may include a plurality of crystalline siliceous molecular sieve materials for the purpose of suppression or removal of menstrual odors.

Fibrous absorbent articles have been known for some time. They incorporate a plurality of fibers arranged in a structure to absorb and retain body fluids. In connection with the present invention, the body fluid of particular concern is menstrual fluid which may generate unpleasant odors.

A variety of proposals have been made in the past as a means to counteract menstrual odors. Such proposals have included the use of perfumes to mask the odors that emanate from the absorbent article. Other proposals include the use of substances to suppress or remove odoriferous compounds that may be generated in the presence of menstrual fluids and the like. These odoriferous compounds may be suppressed by a number of mechanisms including forming a non-odoriferous compound by chemical reaction or by adsorption of the odoriferous compounds into a solid or liquid. For an adsorbent to be effective in deodorizing, especially for odors from body fluids that are characterized as having very low olfactory thresholds, it is essential that the sorbent be capable of removing, in its environment, virtually all the odoriferous compounds regardless of the concentration thereof.

2. Description of the Prior Art

In order to provide a full background for the present invention reference may be made to U.S. Pat. Nos. 3,948,257; 4,795,482; 4,826,497; and 5,364,380; also Registration HI579.

U.S. Pat. No. 3,948,257 is directed to a vulva deodorant system comprising a tampon for insertion into the vagina and a device for retaining a deodorant. The device may include a deodorant in the form of a perfume, powder or the like.

U.S. Pat. No. 4,795,482 is directed to a process for eliminating organic odors and compositions for use therein. The method involves reducing the odors below olfactory detection by contact of the odor producing species with a synthetic crystalline siliceous molecular sieve material.

U.S. Pat. No. 4,826,497 provides fibrous absorption articles having enhanced deodorizing properties by having disposed therein an effective amount of crystalline siliceous molecular sieve having pore diameters of at least about 5.5 Angstroms and a relatively low capacity for adsorbed water. In addition, this patent provides for the inclusion of zeolite particles having a size of less than about 20 micrometers in the deodorizing sieve. The particles are positioned between the exterior surface of the fluid permeable cover of the absorbent article and a baffle provided within the article.

U.S. Pat. No. 5,364,380 provides an absorbent article having a first surface facing the body of a user and a second surface aligned approximately opposite to the first surface. There is also provided a liquid-impermeable baffle and a fluid-permeable cover positioned adjacent to the respective surfaces. In addition, a deodorizing mixture is positioned within the article so as to remain dry for a substantial period of time. The mixture is an anhydrous, non-buffer blend of at least basic and pH neutral odor adsorbing particles.

Registration HI579 provides zeolites having "intermediate" $SiO_2/Al_2O_3$ ratios used in catamenials, diapers and the like to control odors. Such intermediate ratios are described as typically in the range from about 2 to about 10.

It may be the case that when applied appropriately there are particular benefits and advantages to the several inventions described in the aforesaid patents. However, it will be apparent that the present invention provides a key advantage not found in prior art. What has been discovered and recognized is that specific natural zeolites have unique capabilities in that they have the property of controlling and suppressing odor in the presence of moisture. Consequently, a very effective and efficacious fibrous absorbent article, for example, a tampon, can be fabricated in such a way as to capitalize on the natural zeolite's capability for adsorbing odoriferous organic molecules associated with menstrual fluids even in the presence of water that may be present in such fluids.

One of these specific zeolites can be classified as a thermal type 3 clinoptilolite species based on its chemistry and silica/alumina ratio. The zeolite, clinoptilolite, has been discussed in the book entitled Natural Zeolites by O. Gattardi and E. Gall; published by Springer-Verlay, 1985. This thermal behavior, type 3 zeolite is defined as a zeolite capable of undergoing continuous reversible dehydration with only very small lattice contraction, and the lattice is not destroyed so long as temperature remains below 750° C. This zeolite is an off-white clinoptilolite with potassium as the primary exchangeable cation. The presence of this exchangeable cation is believed to be the main influencing factor on the thermal behavior, as set forth in the article cited.

Another zeolite that has been shown to be efficacious is chabasite. This zeolite is a tan mineral with sodium as the primary exchangeable cation. The odor adsorbent efficacy of this zeolite is likely due to its very high surface area (500 $m^2$/gm), the sub micron size (0.2$\mu$) of the individual crystalline structures, and its large pore size. These features combine to provide a more readily accessible lattice resulting in a more rapid rate of odor adsorption.

SUMMARY OF THE INVENTION

Accordingly, it is an object of the present invention to provide a catamenial device or product, such as a tampon, that can be reliably and inexpensively produced and that will efficiently adsorb odors associated with menstrual fluid.

It is another object of the present invention to maximize the effect of a desired amount of odor adsorbent material in a tampon.

It is further object of the present invention to provide the tampon with efficient odor adsorption even in the presence of water or other liquid.

It is a still further object of the present invention to provide a method of incorporating the odor adsorbent material into a tampon.

The above and other objects of the present invention are fulfilled by the feature of a tampon or similar device or product in which there is disposed a natural zeolite of the specific type. Briefly stated, a broad feature of the present invention can be defined as follows: a fibrous absorbent article for absorbing body fluids made up of a fibrous material defining a structure suitable for absorbing the body fluids, and disposed within the structure an effective amount, so as to reduce odors from the body fluids, of a molecular sieve constituted of a natural zeolite of the clinoptilolite or chabasite species comprising SiO2 and Al2O3.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1A:
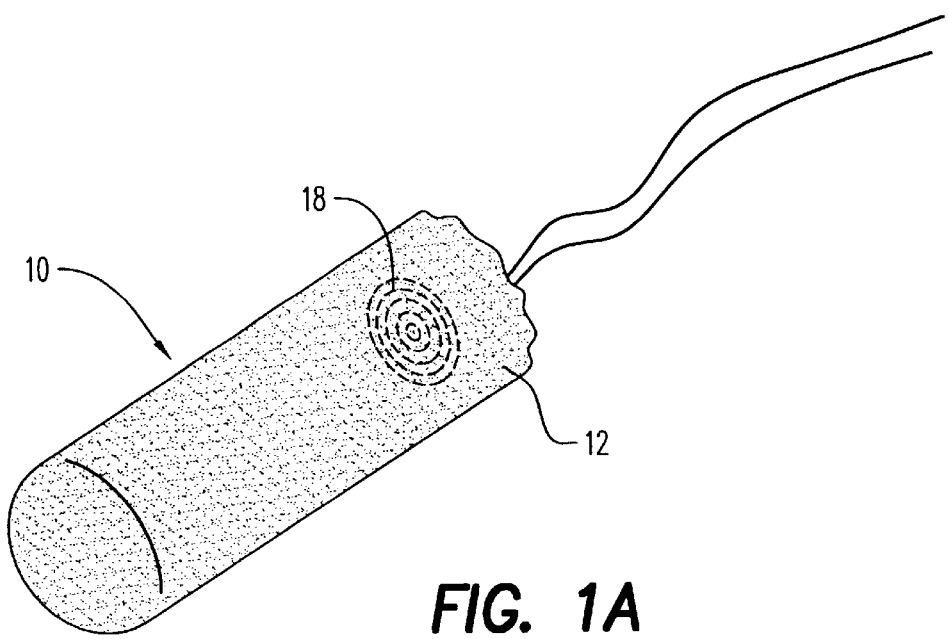
FIG. 1A is a perspective view of a tampon that incorporates the zeolite powder according to the present invention.
Figure 1B:
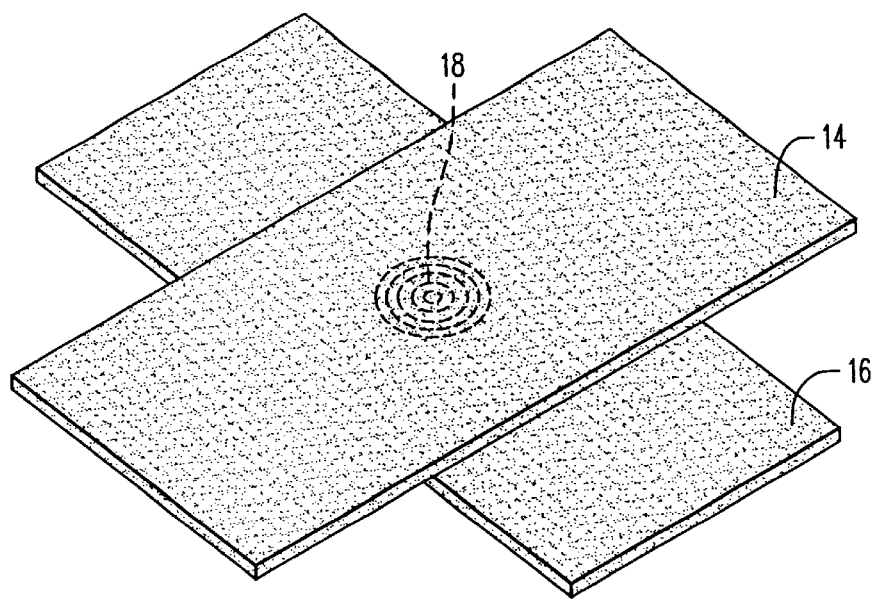
FIG. 1B is a perspective view of the tampon of FIG. 1 prior to assembly.
Figure 2A:
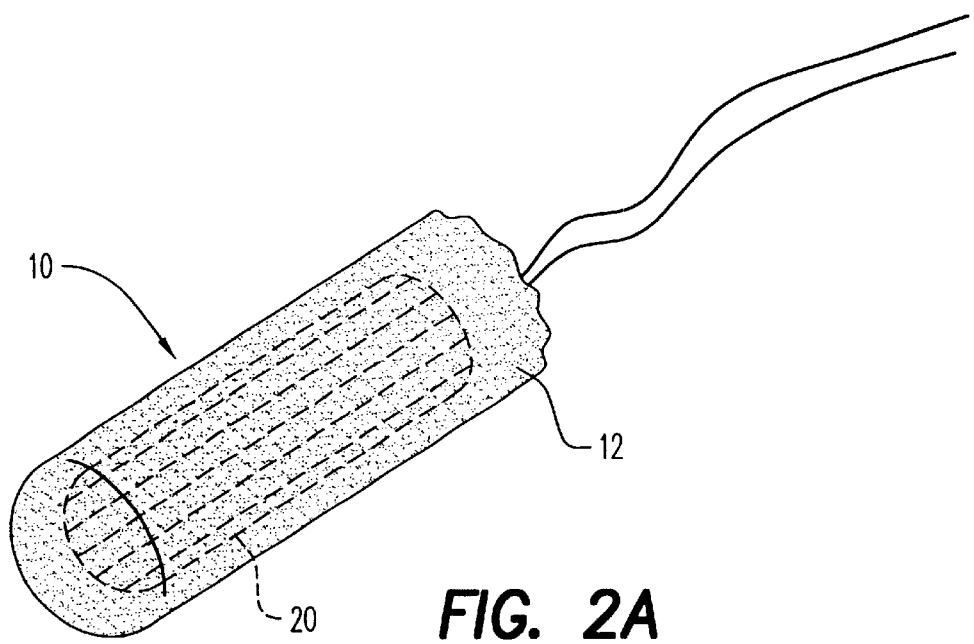
FIG. 2A is a perspective view of a tampon that incorporates the zeolite strip according to the present invention.
Figure 2B:
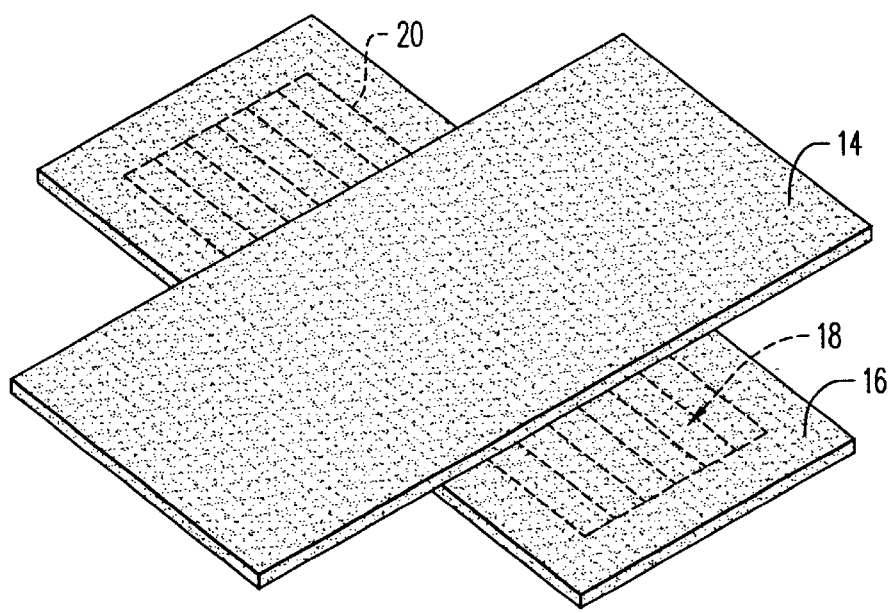
FIG. 2B is a perspective view of the tampon of FIG. 2A prior to assembly.

Before proceeding with the description of the fibrous absorbent article of the present invention in which a special type of zeolite in powdered or granular form is incorporated, it is considered useful first to describe the characteristics of the special type of zeolite.

It will be understood from what has been indicated previously that the zeolite of the present invention is a natural zeolite and is classified as either a thermal type 3 clinoptilolite species (based on the classification assigned in the article cited above) or chabasite species.

One particular form useful in accordance with the present invention is designated CABSORB® ZK406H®, a product marketed by GSA Resources Inc. This material is in off-white clinoptilolite with potassium as the primary exchangeable cation. Potassium is present in an amount of the order of 4.3% of the zeolite.

Another particular form useful in accordance with the present invention is designated CABSORB® ZS500A®, a product marketed by GSA Resources Inc. This material is a tan mineral chabasite with sodium as the primary exchangeable cation. Sodium is present in an amount of the order of 6.7% of the zeolite.

It should be especially noted that these zeolites are partially activated in the processing discussed later herein.

The clinoptilotite species can also be characterized based on its chemistry and silica/alumina ratio which is approximately 5.8:1. As a result of a suitable thermal activation step, a very stable type 3 crystal lattice is achieved. Of significance is that with potassium as the primary cation, a stable lattice is formed which has an enhanced capacity for adsorption of organic molecules even in the presence of water (or other liquids).

The following is a particular specification for the molecular sieve material, i.e. the natural zeolite in the form of thermal type 3 clinoptilolite, useful in the present invention.

CABSORB ® ZK406H ®
Potassium Aluminosilicate
Natural Clinoptilolite

TYPICAL PROPERTIES

| | |
|---|---|
| Form | Granules |
| Color | Gray |
| Pore Diameter | 4.0 Angstroms |
| Pore Volume | 15% |
| Specific Surface Area | 40 m$^2$/g. |
| Bulk | 53–66 lbs/ft$^3$ |
| | 783–1054 Kg/m$^3$ |
| Solid Density | 87 lbs/ft$^3$ |
| | 1390 Kg/m$^3$ |
| Alkali Stability | pH of 7–10 |
| Acid Stability | pH of 3–7 |
| Thermal Stability | 1202 degrees F. |
| | 650 degrees C. |
| Ion Exchange Capacity | 1.65 milliequivalents/g |

TYPICAL CHEMICAL ANALYSIS

| SiO$_2$ | Al$_2$O$_3$ | Fe$_2$O$_3$ | CaO | MgO | Na$_2$O | K$_2$O | MnO |
|---|---|---|---|---|---|---|---|
| 69.1 | 11.9 | 0.7 | 0.7 | 0.4 | 0.8 | 3.8 | 0.5 |

Besides potassium as the primary exchangeable cation, this particular zeolite has the following exchangeable cations:

| | | | | | | | | | |
|---|---|---|---|---|---|---|---|---|---|
| Rb+ | Na+ | Ba+$^2$ | Mg+$^2$ | Li+ | Ag+ | Sr+$^2$ | Fe+$^3$ | K+ | Cd+$^2$ |
| Cu+$^2$ | Co+$^3$ | Cs+ | Pb+$^2$ | Ca+$^2$ | Al+$^3$ | NH$_4$+ | Zn+$^2$ | Hg+$^2$ | Cr+$^3$ |

Of the above exchangeable cations, the amount of calcium, magnesium and sodium and their ratio to each other appears important. As set forth above, the amount of calcium (Ca) is 0.7, the amount of magnesium (Mg) is 0.4 and the amount of sodium (Na) is 0.8.

The chabasite species can be characterized based on its chemistry and silica/alumina ratio which is approximately 4:1. As a result of a suitable activation step, which is the same step as for clinoptilolite, a very active material is achieved. Crystalline water in the lattice structure is driven off creating a certain amount of internal access making the pores more accessible for odor adsorption. The following is a particular specification for the chabasite species, useful in the present invention.

TYPICAL PROPERTIES

| | |
|---|---|
| Form | Powder or Granules |
| Color | Light Brown(Dry Brightness 43) |
| Ring Member | 8 |
| Crystal Size-Chabazite | Less than 1 micron |
| Crystallinity | +90% |
| Density | 1.73 g/cm$^3$ |
| Pore Size | 4.1 by 3.7 Angstroms |
| Effective Pore Diameter | 4.3 Angstroms |
| Cavity Size | 11.0 by 6.6 Angstroms |
| Total Pore Volume | .468 cm$^3$/g |
| Surface Area | 520.95 m$^2$/g |
| Crystal Void Volume | .47 cm$^3$/cm$^3$ |
| Packing Density | Approx. 577 kg/m$^3$ (36 lbs/ft$^3$) |
| SiO$_2$/Al$_2$O$_3$ Ratio | Approx. 4:1 |
| MOH's Hardness | 4–5 |

| | -continued |
|---|---|
| Moisture as packaged | Less than 10% by weight |
| Stablility | pH of 3 through 12 |
| Ion Exchange Capacity | 2.50 meq/g |

TYPICAL CHEMICAL ANALYSIS
(equilibrated at 20° C. and 40% relative humidity)

| $SiO_2$ | $Al_2O_3$ | $Fe_2O_3$ | CaO | MgO | NaO | K2O | LOI | Dominant Cation |
|---|---|---|---|---|---|---|---|---|
| 54.6 | 14.9 | 2.28 | 0.22 | 0.60 | 6.67 | 0.90 | 19.4 | Na |

EXCHANGE SELECTIVITIES

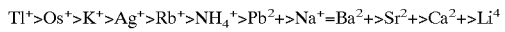

$Tl^+>Os^+>K^+>Ag^+>Rb^+>NH_4^+>Pb^2+>Na^+=Ba^2+>Sr^2+>Ca^2+>Li^4$

EXCHANGE OF HEAVY METAL IONS

Weight Percent of Heavy Metals Retained in anhydrous CABSORB after Ion Exchange from a 0.10mg/ml solution $AgNO_3$, $Pb(NO_3)_2$, $CoSO_4$ and a 0.025. mg/ml solution of $CuSO_4$ at the initial Mitial pH indicated for each solution.

| Ag | | Pb | | Cu | | Go | |
|---|---|---|---|---|---|---|---|
| pH | wt % | pH | wt % | pH | wt % | pH | wt % |
| 5.30 | 21.85 | 3.80 | 5.27 | 3.43 | 3.17 | 2.91 | 2.32 |

Before proceeding further it is thought useful to provide certain general information concerning zeolites and their use. Zeolites are minerals with unique physical and chemical characteristics. Their chemical structure classifies them as hydrated alumino silicates. The silicates include hydrogen, oxygen, aluminum and silicon, arranged in an interconnecting crystal lattice structure. The arrangement of these elements in a zeolite crystal creates a framework silicate structure with consistent diameter connecting channels (pores) that vary in size from 2.5 to 5.0 angstroms, depending on the zeolite mineral. This structure allows zeolites to perform the following functions consistently in a broad range of chemical and physical environments: gas adsorption, that is, the ability to selectively adsorb specific gas molecules; water adsorption/desorption which is the ability to reversibly adsorb/desorb water without any chemical or physical change in the zeolite matrix; and ion exchange, which is the ability to exchange inherent cations for other cations on the basis of ion selectively.

In the particular clinoptilolite zeolite of the present invention, the molecular sieve experiences reversible dehydration when subject to a wide temperature range from zero to 600 degrees C. At the same time, this zeolite experiences a very small crystal lattice contraction, thus maintaining the pore structure and thereby enhancing odor adsorbent properties.

It will be understood that the crystalline siliceous molecular sieve or sieve material of clinoptilolite or chabasite species of zeolites, as a component of the present invention, may be in any suitable form, such as zeolite powder strip, a zeolite granule strip, or a slurry or suspension of zeolite powder.

As noted previously, the molecular sieve may typically be utilized in its granular form with each granule particle size between about 400 to about 600 microns. However in the preferred embodiment, the clinoptilolite or chabasite species zeolite is pulverized into a powder in which each particle is about −325 mesh, which is about 8.5 microns. For example in this preferred embodiment, the rock taken from the mine is coarsely crushed and passed through a particle dryer at 250 to 300 degrees F. The particles are screened and sorted according to particle size. The small particles sizes are then collected and then run through an air classification system to further sort. As stated above, the desired particle size of the zeolite powder particles is −325 mesh, which is approximately 8.5 microns ($\mu$).

The zeolite granules or zeolite powder particles may be any convenient shape, e.g. spheres, cylinders or the like.

As shown in FIGS. 1A, 1B, 2A and 2B, the fibrous absorbent article 10 comprises fibrous material 12 capable of absorbing body fluids such as catamenial fluids and the like. The fibrous material 12 may be arranged to form a woven or non-woven structure. The fibrous absorbent article 10 is, in the particular example of the Figures, a tampon which has a well-known cylindrical shape and may consist of a number of fibrous layers, such as inner layer 14 and outer layer 16. As another example, a sanitary napkin may form the absorbent article and may consist of a plurality of fibrous absorption fabrics.

As shown in the, Figures, the crystalline siliceous molecular sieve 18 is disposed or incorporated in the fibrous absorbent article 10. This incorporation may be accomplished within the structure between the layers 14 and 16 that form the tampon. The amount of the material 18 should be sufficient to significantly reduce, if not essentially eliminate, the odors from the menstrual fluid. In the case of the tampon illustrated, as little as about 0.02 grams of zeolite has been found to effectively remove odors.

It should be noted that the amount or amounts of siliceous molecular sieve 18 used in the fibrous absorption article may vary depending upon the size of the tampon and, perhaps, cost considerations. However, it is believed that in a normal tampon about 0.12 grams of zeolite can be used. In experimentation, as high as about 0.93 grams of zeolite can be used. In the preferred embodiments, it is believed that the zeolite in the zeolite strip (powder or granule) should have no less than 0.030 grams, whereas the amount of zeolite in the slurry (powder) should be no less than about 0.018 grams.

It was suggested above in connection with the description of tampon 10 presented in the Figures that the molecular sieve 18 could simply be disposed between layers 14 and 16 in one preferred way. However, the molecular sieve 18 can be loosely dispersed within a batte or tissue containing fibrous material, although it is generally preferred that the sieve be sufficiently immobilized in the fibrous absorbent for ease of manufacturing.

The method of incorporating the zeolites or sieve into a tampon is unique, thereby constituting an important aspect of the present invention. In a first method, a strip containing the zeolite either as granules or powder was employed. In a second method, a liquid suspension or slurry of powder was involved.

Of the first method, the strip containing the zeolite as a powder is preferred over the strip containing the zeolite as granules.

In the strip 20 (FIG. 2B) containing the zeolite as a powder, the zeolite powder (−325 mesh, 8.5 microns) is incorporated in a liquid binder. The amount of zeolite added to the binder is sufficient to provide approximately 51g/m² in the final strip. A non-woven web is passed through the binder containing the zeolite after which the excess binder is removed and the web is dried, rolled and then slit into strips. These strips with zeolite are cut to an appropriate size and incorporated into the tampon. In certain tampons, such a zeolite strip is inserted between two absorbent pads prior to the tampon being formed.

Figures 3, 4:
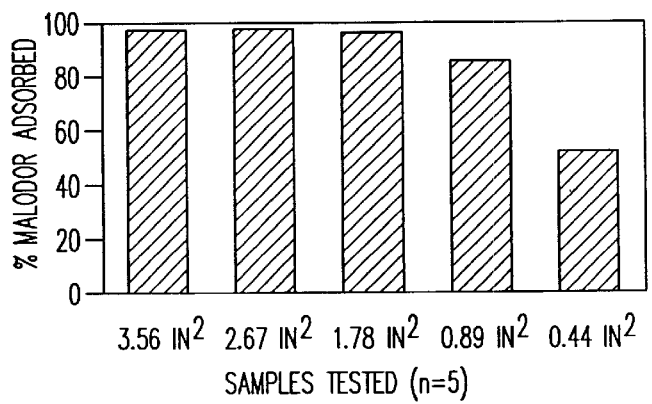
FIG. 3 is a table that provides odor adsorption test results of zeolite powder disposed in a strip.
FIG. 4 is a graph corresponding with the table of FIG. 3.

The 51g/m² zeolite in the strip equates to 0.117 gram(g) zeolite in a strip cut to the size, 1½×2⅜ inches (3.56 in.²) incorporated into the tampon. The 0.117 gram zeolite has been found to give more than adequate odor adsorbent efficacy as indicated in FIG. 3. As shown in FIG. 4, tampons with these strips (3.56 in.²) with 0.117 gram zeolite) placed in a market research test, were also shown to give odor protection.

In the strip 20 (FIG. 2B) containing the adsorbent material as granules, each zeolite granule, preferably 30×40 mesh, is distributed on a non-woven web. The zeolite particles and non-woven web are then bonded to a second non-woven web such that the zeolite granules are sandwiched between the two non-woven webs. The web containing the zeolites is then cut into strips and the strips are incorporated into tampons as previously described.

In the second, liquid suspension/slurry method, the zeolite powder (−325 mesh, 8.5 microns) is suspended in a liquid along with a suspension aid. The use of the suspension aid is critical for two reasons. The first reason is that the suspension aid maintains the powder in suspension during manufacturing, so that it is possible to dispense a given amount of the material. The second reason is that the suspension aid, when it dries, helps to adhere the powder to the absorbent web of the tampon, thus immobilizing the zeolite powder. The liquid suspension containing the zeolite and the suspension aid is dispensed on the absorbent pads of the tampon prior to formation of the tampon.

Figures 5, 6:
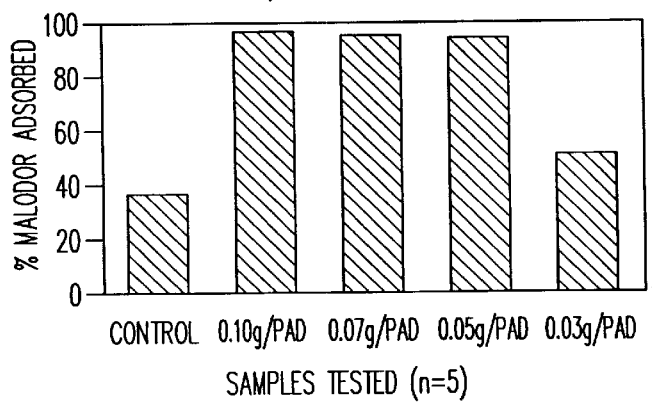
FIG. 5 is a table that provides odor absorption test results of zeolite powder which is added to the tampon as a liquid suspension.
FIG. 6 is a graph corresponding with the table of FIG. 5.

It has been found that suspensions could be made that varied in viscosity and, thus, ease of dispensing. This was achieved by varying the amount of zeolite added or by varying the amount of the suspension aid added. One suspension that was found to be adequate for dispensing contained 36.6% zeolite and 2.4% Veegum (suspension aid) suspended in 61% water. The odor adsorbing efficacy test showed that as little as 0.05 gram of the 36.6% zeolite slurry (0.018 gram zeolite) was efficacious as shown in FIG. 5.

The odor adsorbent tampon scored extremely well in tests. Test results for both methods are presented as FIGS. 3 and 4, and FIGS. 5 and 6, respectively. From these Figures, the absorption benefit of the present invention will be thoroughly appreciated.

In vitro test of tampon malodor adsorption determined by GC/headspace was conducted to determine the odor adsorbent efficacy of the zeolite. This method used Gas Chromatograph/head space analysis to detect the presence of a known amount (2 μl.) of a synthetic vaginal malodor. Test samples, identified as a zeolite strip or 1 in.2 rayon non-woven pads with a known amount of the 36.6% zeolite slurry, were introduced to the system. The amount of malodor adsorbed by the test samples was determined. Both the strip containing the zeolite and the liquid suspension were effective in adsorbing or eliminating a synthetic vaginal malodor. The material tested adsorbed 90% or greater of the synthetic vaginal malodor present. As shown in FIGS. 3 and 5, as little as 0.05 grams incorporated in the strip and as little as 0.018 gram zeolite powder added to the tampon as a suspension, eliminated 95% of a known quantity (2 μl.) of a synthetic vaginal malodor. In fact, as little as 0.029 grams incorporated into the strip adsorbed 86% of the malodor. This was achieved with both the clinoptilolite and chabasite species. The chabasite species odor adorbing efficacy is comparable, however chabasite is more expensive and the color is believed undesirable in a tampon.

There was conducted an in vivo test of 300 women among a nationally balanced panel of tampon users 13 to 49 years of age to determine whether the tampon with clinoptilolite was perceived as effective in reducing odors associated with tampon use. Women were given such tampons (with the tampon size depending on the woman's flow needs) with the clinoptilolite zeolite strips (1½ by 3⅜ inches, with 56 g/m² zeolite approximately equal to 0.117 gram zeolite/strip) formed into the tampon. The women used these tampons as they normally would during menstruation.

217 women responded. The results showed that the odor adsorbing properties of the tampon tested were extremely well accepted. There was virtually no criticism of deodorancy or lack of deodorancy protection. The test results indicated that the women tested believe that the tested tampon protects against odor and delivers a fresh clean feeling.

Over 80% percent of the respondents had a total positive rating, namely "likes extremely well" or "likes very well". Apparently, the respondents like the fact that the tested tampons adsorb odor, yet have no odor or fragrance.

The present invention having been thus been described with particular reference to the preferred forms thereof, it will be obvious that various changes and modifications may be made therein without departing from the spirit and scope of the present invention as defined in the appended claims.

What is claimed is:

1. A catamenial article for absorbing body fluids comprising:
    a catamenial fibrous material suitable for absorbing the body fluids; and
    a molecular sieve disposed within the fibrous material to adsorb odors from the body fluids, wherein said molecular sieve has a natural zeolite of the clinoptilolite species with potassium as a primary exchangeable cation.

2. The fibrous article as defined in claim 1, wherein said zeolite is a thermal type 3 clinoptilolite.

3. The fibrous article as defined in claim 2, wherein said thermal type 3 clinoptilolite is a potassium aluminosilicate natural clinoptilolite.

4. The fibrous article as defined in claim 1, wherein said potassium is present in an amount of the order of 4.3% of the zeolite.

5. The fibrous article as defined in claim 1, wherein said zeolite has a solid density of 87 lbs/ft³.

6. The fibrous article as defined in claim 1, further comprising one or more secondary exchangeable cations.

7. The fibrous article as defined in claim 6, wherein the one or more secondary exchangeable cations is selected from the group consisting of calcium, magnesium and sodium.

8. The fibrous article as defined in claim 1, wherein said molecular sieve experiences reversible dehydration when subject to a wide temperature range from zero to 600 degrees C., while experiencing a very small crystal lattice contraction.

9. The fibrous article as defined in claim 1, wherein said molecular sieve has a natural crystalline aluminosilicate with a high silica to aluminum ratio, and wherein said molecular sieve contracts only slightly on activation so that internal surfaces of said molecular sieve remain open and available to attract odoriferous molecules thereby insuring good odor adsorption within the pores.

10. The fibrous article as defined in claim 1, wherein the effective amount of said molecular sieve disposed in the fibrous article is no less than about 0.018 grams.

11. The fibrous article as defined in claim 1, wherein the effective amount of said molecular sieve disposed in the fibrous article is no less than about 0.030 grams.

12. The fibrous article as defined in claim 1, wherein the effective amount of zeolite in the fibrous article is about 0.12 grams.

13. A catamenial article for absorbing body fluids comprising:

a catamenial fibrous material suitable for absorbing the body fluids; and a molecular sieve disposed within the fibrous material to adsorb odors from the body fluids, wherein said molecular sieve has a natural zeolite of the chabasite species with sodium as a primary exchangeable cation, said natural zeolite having a solid density of 108 lbs/ft$^3$.

14. The fibrous article as defined in claim 13, wherein said chabasite is a sodium aluminosilicate.

15. The fibrous article as defined in claim 13, wherein said sodium is present in an amount of the order of 6.7% of the zeolite.

16. The fibrous article as defined in claim 13, further comprising one or more secondary exchangeable cations.

17. The fibrous article as defined in claim 16, wherein the one or more secondary exchangeable cations is selected from the group consisting of calcium and magnesium.

* * * * *